United States Patent
Cadalen

(10) Patent No.: US 9,581,558 B2
(45) Date of Patent: Feb. 28, 2017

(54) METHOD FOR DETERMINING AT LEAST ONE PIECE OF INFORMATION REPRESENTATIVE OF A PHASE FRACTION OF A FLUID IN A PIPE

(75) Inventor: Sebastien Cadalen, Aubervilliers (FR)

(73) Assignee: Geoservices Equipements, Roissy en France (FR)

(*) Notice: Subject to any disclaimer, the term of this patent is extended or adjusted under 35 U.S.C. 154(b) by 610 days.

(21) Appl. No.: 13/581,462

(22) PCT Filed: Feb. 28, 2011

(86) PCT No.: PCT/EP2011/052912
§ 371 (c)(1),
(2), (4) Date: Oct. 2, 2012

(87) PCT Pub. No.: WO2011/104380
PCT Pub. Date: Sep. 1, 2011

(65) Prior Publication Data
US 2013/0034206 A1    Feb. 7, 2013

(30) Foreign Application Priority Data
Feb. 26, 2010  (FR) ..................... 10 51405

(51) Int. Cl.
G01N 23/12    (2006.01)
G01N 33/28    (2006.01)

(52) U.S. Cl.
CPC ......... *G01N 23/12* (2013.01); *G01N 33/2823* (2013.01)

(58) Field of Classification Search
CPC ................. G01N 23/12; G01N 23/06

USPC ............... 378/51, 53, 66; 702/24, 28
See application file for complete search history.

(56) References Cited

U.S. PATENT DOCUMENTS

| | | | |
|---|---|---|---|
| 4,665,486 A | 5/1987 | Schultz | |
| 5,654,551 A * | 8/1997 | Watt et al. | 250/356.1 |
| 5,689,540 A * | 11/1997 | Stephenson et al. | 378/53 |
| 5,854,820 A | 12/1998 | Slijkerman et al. | |
| 6,097,786 A * | 8/2000 | Groves et al. | 378/53 |
| 7,684,540 B2 * | 3/2010 | Groves et al. | 378/53 |
| 2004/0046115 A1 * | 3/2004 | Berard et al. | 250/256 |
| 2007/0144268 A1 * | 6/2007 | Atkinson | 73/861.63 |

FOREIGN PATENT DOCUMENTS

GB    2410792    8/2005

OTHER PUBLICATIONS

First Office Action dated Aug. 18, 2014 for the Chinese Patent Application No. 201180015457.4.

* cited by examiner

*Primary Examiner* — Jack Berman
(74) *Attorney, Agent, or Firm* — Cameron R. Sneddon

(57) ABSTRACT

A method is presented for determining at least one piece of information representative of a phase fraction of a fluid in a pipe. The method comprises the estimation of a number of counts received in each measuring interval based on each piece of representative information determined at a preceding iteration, then calculating a residual comprising a first criterion calculated from probabilities using a given statistical law to measure, for each energy, the number of counts measured in each interval, the given statistical law being parameterized based on the number of estimated counts.

21 Claims, 6 Drawing Sheets

METHOD FOR DETERMINING AT LEAST ONE PIECE OF INFORMATION REPRESENTATIVE OF A PHASE FRACTION OF A FLUID IN A PIPE

CROSS-REFERENCE TO RELATED APPLICATION

The present application is based on and claims priority to French Patent Application No. 1051405, filed Feb. 26, 2010.

TECHNICAL FIELD

The present invention relates to a method for determining at least one piece of information representative of a phase fraction of a multiphase fluid circulating in a pipe.

Such a method is intended for example to be implemented in a multiphase flowmeter. Such a flowmeter is in particular used to characterize the flow of a fluid extracted from a well formed in the subsoil, such as a hydrocarbon production well.

BACKGROUND ART

During the production of the well, it is known to measure the flow rate of fluid extracted from the well to be able to monitor the quantity and quality of the production. In particular, it is frequently necessary for the operator of the well to determine the overall flow rate of fluid flowing through the pipe, and if possible, the individual volume flow rates of each phase flowing in the pipe.

To determine these values, it is necessary to estimate the volume fraction of gas contained in the multiphase fluid, often referred to as "gas hold up," and the proportion of aqueous phase present in the liquid at any moment.

To estimate these parameters, it is known to determine the relative areas occupied by each of the gas phase, the oily liquid phase and the aqueous liquid phase on a section of the pipe. To that end, a radioactive source is placed opposite a wall of the pipe to emit gamma photons at typically one or more energy levels.

The gamma photons are then oriented transversely through the fluid flowing in the pipe. A detector is placed opposite the source, opposite the pipe to collect and count the photons that pass through the multiphase fluid and determine their energy. The count number received at each energy is measured at a high frequency, for example with a sampling pitch in the vicinity of 20 ms. This makes it possible to calculate the lineic fraction of the gas, i.e. the ratio between the length of the gaseous phase crossed and the internal diameter of the pipe.

Due to the nature of the radioactive source, there is a natural statistical dispersion of the number of counts measured, even in the case where the measured fluid is static. The measurement uncertainty resulting from this dispersion can be reduced significantly by increasing the integration time.

However, in practice, the multiphase fluid circulates in the pipe at a high flow rate. This fluid is generally turbulent and sometimes has structural irregularities, for example gas bubbles in liquid, or plugs in gas that make the flow unstable.

Measuring the number of gamma photon counts remains an effective way to measure the phase fractions, regardless of the state of flow. However, in a dynamic state, the number of counts cannot be significantly averaged to reduce the statistical noise, since the nature of the flow can vary quite rapidly.

Subsequently, in certain cases, the results obtained directly based on count measurements done in a dynamic state have significant fluctuations.

To resolve this problem, U.S. Pat. No. 5,854,820 proposes a method in which the statistical fluctuations of the measured numbers of counts are compensated by an algorithm making it possible to model the attenuations and compare them to the measured attenuation. A statistical residual is calculated and is minimized to estimate the fractions.

Such a calculation increases the precision of the measurement, but can still be improved, in particular to optimize the determined values of the gas content levels and the proportion of water, in particular when these values are close to their physical boundary values.

One aim of the present disclosure is therefore to provide a method for calculating phase fractions that are more precise, even when the values of the measured fractions are close to their physical boundaries and/or it is not possible to significantly average the measured numbers of counts, given the dynamic nature of the flow.

BRIEF SUMMARY OF THE DISCLOSURE

To that end, the present disclosure relates to a method of the aforementioned type, characterized in that it comprises the following steps:
(a) emitting a number of gamma photon counts at at least one energy through the fluid; and
(b) measuring a number of counts received for each energy, after passage in the fluid;
(c) dividing a given measuring period into a plurality of measuring intervals in which each piece of representative information is assumed to be constant;
(d) choosing an initial value of the or each piece of representative information in each interval;
(e) determining the or each piece of representative information in each interval through successive iterations until a convergence criterion is verified, each iteration comprising:
($e_1$) estimating a number of counts received at each energy in each interval based on the or each piece of representative information determined at a preceding iteration,
($e_2$) calculating a residual comprising a first criterion calculated from probabilities according to a given statistical law to measure, for each energy, the number of counts measured at each interval, the given statistical law being parameterized based on the number of counts estimated in step ($e_1$) at each interval;
($e_3$) determining new values of the or each piece of representative information to minimize the residual;
step (e) including, at each iteration,
($e_4$) calculating the average, for each energy, of an estimated number of counts for each interval based on the representative information determined in a preceding iteration, the residual calculated in step ($e_2$) comprising a second criterion calculated from probabilities according to a given statistical law to measure, for each energy, an average number of counts, the given statistical law being parameterized based on the average calculated in step ($e_4$).

The method according to the disclosure can comprise one or several of the following features, considered alone or according to all technically possible combinations:

for each energy, the average count number is an average number of counts in an empty pipe measured during a calibration step at each energy, in the absence of fluid in the pipe, the step including the calculation of the average, for each energy, of the number of counts in an empty pipe estimated for each interval based on the representative information determined in a preceding iteration;

the representative information is respectively the lineic fraction of gas according to a diameter of the pipe and the volume fraction of water in the liquid phase present in the multiphase fluid;

the statistical law is a Poisson law;

the residual is calculated using the formula:

$$f_{le} + f_{he} + \omega \cdot (m_{le} + m_{he})$$

in which $f_{le}$ and $f_{he}$ are the first criteria calculated at the first energy and the second energy, respectively, $m_{le}$ and $m_{he}$ are the second criteria calculated at the first energy and the second energy, respectively, and $\omega$ is a weight coefficient;

wherein the method comprises scanning the raw representative information obtained at the end of step (e) at each interval to determine the raw representative information coming from a given interval of physical values, then blocking at least one piece of raw representative information coming out of the interval of physical values so that its value remains equal to one end of the interval;

The method may further comprise a step (f) for determining each piece of representative information in each interval through successive iterations until verification of a convergence criterion, each iteration comprising:

($f_1$) estimating a number of counts received at each energy in each interval based on the representative information determined at a preceding iteration from representative information obtained after blocking the or each piece of locked representative information;

($f_2$) calculating a residual comprising a third criterion calculated from probabilities according to a given statistical law to measure, for each energy, the number of counts estimated at each interval from representative information obtained without blocking at the end of step (e), the given statistical law being parameterized based on the number of counts estimated in step ($f_1$) at each interval;

the blocking step includes the selection of at least a first group of representative information having a value situated outside the interval of physical values given, without blocking a second group of determined representative information having a value situated outside the interval of given physical values, then carrying out step (f);

the or each piece of locked representative information is chosen based on a criterion representative of the count transfer resulting from blocking the representative information;

calculating the third criterion comprises calculating a count transfer probability coefficient resulting from blocking at least one piece of representative information in each interval at each energy to weight each probability calculated in step ($f_2$);

the step for dividing the given period into a plurality of intervals comprises:

($c_1$) for each interval, determining a beginning of an interval, then calculating, for successive measuring moments moving away from the beginning of the interval, at least one difference between at least one statistical magnitude calculated from the number of counts measured between the beginning of the interval and the measuring moment after the beginning of the interval and the same statistical magnitude calculated based on a known statistical law, until a criterion determined based on said difference is greater than a determined value, the measuring moment in progress then constituting the beginning of another interval, ($c_2$) calculating the average of the number of counts measured at each energy at each measuring moment ($t_r$) in the interval, the average of the number of measured counts defining the number of counts measured in the interval;

($c_3$) repeating steps ($c_1$) and ($c_2$) to define the other interval from the moment following the end of the interval.

the statistical magnitude comprises the variance and/or covariance of the number of counts measured at each measuring moment between the beginning of the interval and the subsequent measuring moment;

the statistical law is a Poisson law, the statistical magnitude being calculated from the Poisson law;

determining the criterion comprises calculating at least the difference:

$$\left[ \frac{V_k - V_k^0}{\sigma_{V_k}} \right]$$

where k is the energy, $V_k$ is the variance of the number of measured counts between the beginning of the interval and the measuring moment after the beginning of the interval, $V_k^0$ is the variance calculated from the statistical law, and $\sigma_{V_k}$ is the standard deviation calculated from the statistical law.

The disclosure also relates to a method for measuring a fluid circulating in a pipe, the method comprising the following steps:

emitting a number of gamma photon counts at at least one energy through the fluid, and measuring a number of counts received for each energy, after passage in the fluid, dividing a given measuring period into a plurality of intervals, comprising:

($c_1$) for each interval, determining the beginning of the interval, then calculating, for successive measuring moments moving away from the beginning of the interval, at least one difference between at least one statistical magnitude calculated from the number of counts measured between the beginning of the interval and the measuring moment after the beginning of the interval and the same statistical magnitude calculated based on a known statistical law, until a criterion determined based on said difference is greater than a determined value, the measuring moment in progress then constituting the beginning of another interval;

($c_2$) calculating the average of the number of counts measured at each energy at each measuring moment in the interval, the average of the number of counts measured defining the number of counts measured in the interval;

($c_3$) repeating steps ($c_1$) and ($c_2$) to define the other interval.

This method does not necessarily comprise steps (d) and (e) above. It can comprise one or several of the above features, considered alone or according to all technically possible combinations.

BRIEF DESCRIPTION OF THE DRAWINGS

The disclosure will be better understood upon reading the description that follows, provided solely as an example and done in reference to the appended drawings, in which.

DETAILED DESCRIPTION

In all of the following, the terms "upstream" and "downstream" refer to the normal direction of circulation of a fluid in a pipe.

Figure 1:
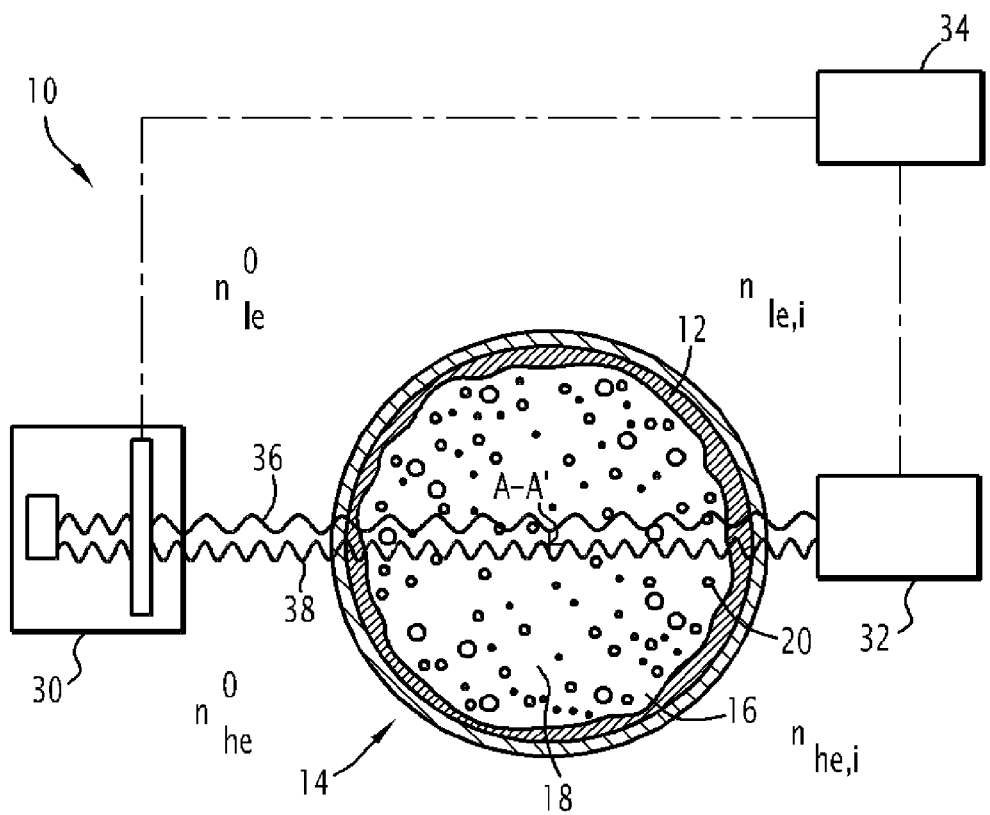
FIG. 1 depicts a diagrammatic view, in cross-section along a median plane of a first measuring device to implement the method according to certain embodiments of the present disclosure.

FIG. 1 illustrates a device 10 for measuring phase fractions of a fluid 12 circulating in a pipe 14 of a fluid exploitation installation such as a hydrocarbon production well. The fluid 12 comprises a gaseous phase, an oily liquid phase and an aqueous liquid phase.

The device 10 is intended to measure dynamically, at any moment, a first piece of information representative of the properties of the fluid, constituted by the lineic fraction of gas formed by the ratio $\Gamma_g$ of the gaseous phase length passed through to the internal diameter of the pipe. The ratio $\Gamma_g$ can be used to calculate the gaseous phase area fraction to the total cross-section occupied by the fluid 12, designated by the term "gas hold up" (GHU).

The device 10 is also intended to measure, at any moment, the ratio of the volume fraction of the liquid aqueous phase in the liquid phase, designated by the term W.

The device 10 is for example integrated within a multiphase flowmeter comprising a means for calculating the flow rates of fluid circulating in the pipe 14 based on fractions $\Gamma_g$, and W measured using the device 10.

The fluid 12 circulating in the pipe 14 can have different flow regimes. In the example illustrated in FIG. 1, the fluid 12 forms an annular flow comprising an essentially liquid annular jacket 16, a gaseous core 18 circulating at the heart of the jacket 16 and drops of liquid 20 circulating in the gaseous core 18. Other flow regimes can also be measured by the device 10 according to certain embodiments of the present disclosure, such as a regime with plugs, for example.

The pipe 14 extends vertically, for example, at the outlet of a hydrocarbon exploitation installation well (not shown). The fluid 12 circulates in the pipe 14 along a substantially vertical axis A-A' opposite the pipe.

The device 10 is for example placed in a section of the pipe 14 defining a venturi.

The device 10 includes a source 30 of gamma photon emissions, and a detector 32 for detecting receipt of the gamma photons after their passage through the fluid 12 contained in the pipe 14, the source 30 and the detector 32 being situated on either side of the pipe 14 along a diameter thereof.

The device 10 also comprises a calculation and control unit 34, and probes (not shown) for measuring the temperature and pressure in the pipe 14.

Figure 2:
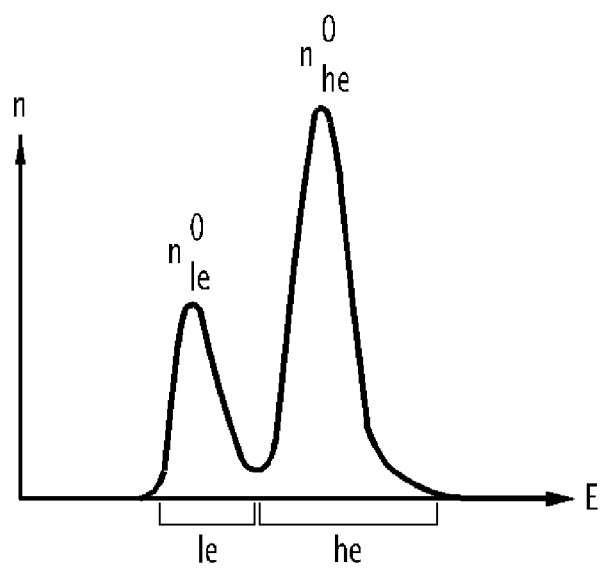
FIG. 2 depicts an illustration of the emission spectrum of the gamma photons created by the device of FIG. 1.

As illustrated by FIG. 2, the source 30 is capable of emitting two beams of gamma rays at different energies, i.e. a low energy (le) beam 36 of gamma photons and a high energy (he) beam 38 of gamma photons.

The number of counts per unit of time emitted by the source 30 is shown diagrammatically in FIG. 2 as a function of the energy of each photon. The photons corresponding to each energy he, le are those included in the respective energy windows he, le.

The gamma photons emitted by the source 30 pass through the fluid 12 transversely between the source 30 and the detector 32.

The detector 32 is capable of detecting, at a given sampling pitch p, the gamma photons having passed through the fluid and determining their energy. This pitch p is in the vicinity of 20 ms.

The calculation and control unit 34 is capable of measuring, at each measuring moment at measuring pitch p, the number of counts of low energy photons $n_{le,p}$ collected at each moment by the detector 32 and the number of counts of high energy photons $n_{he,p}$ collected at each moment by the detector 32, as a function of predefined energy windows.

The calculation unit 34 is capable of carrying out the method according to at least one embodiment of the present disclosure. To that end, it also contains a model for computing representative information $\Gamma_g$ and W determined at each moment.

Figure 4:
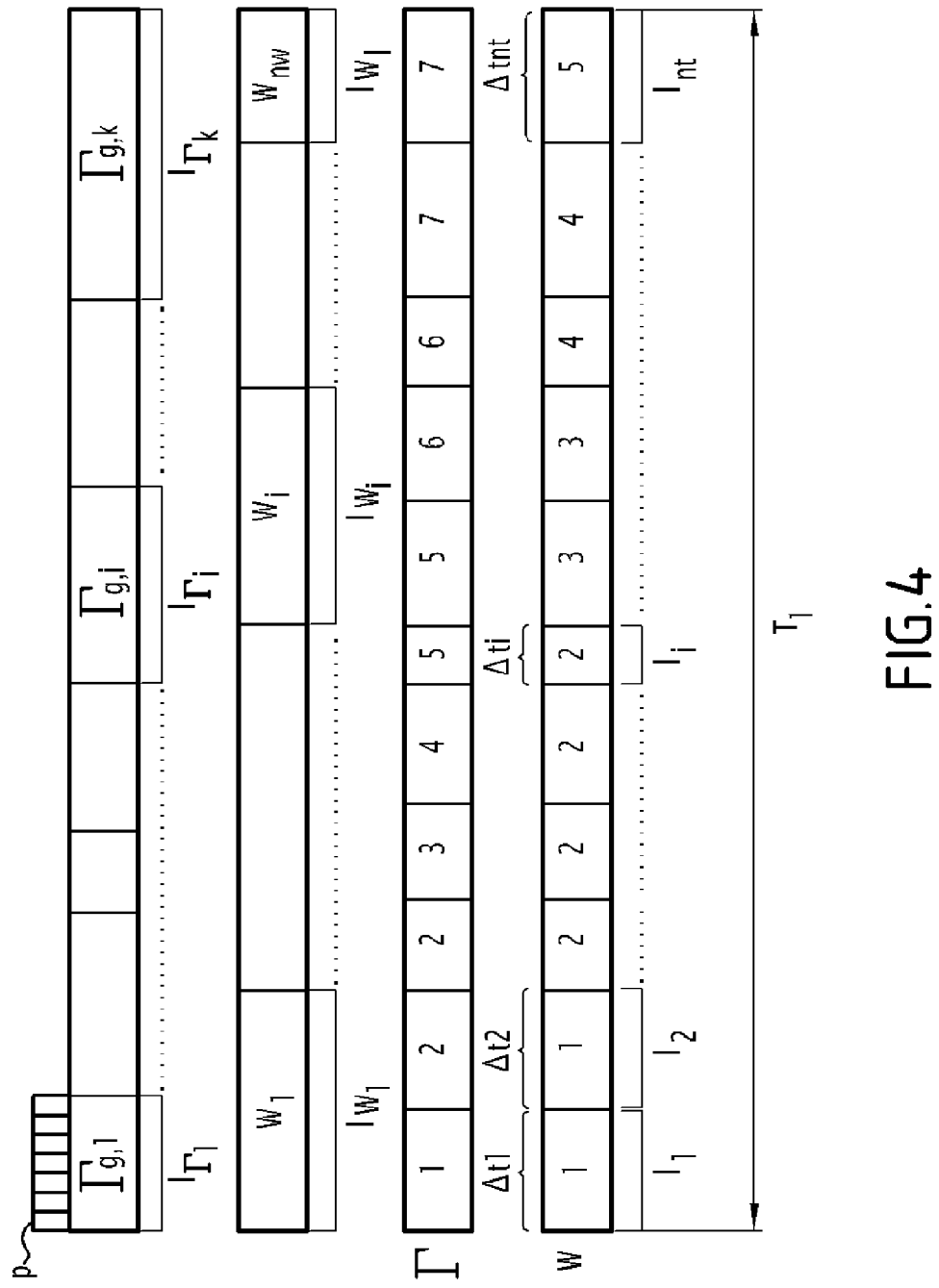
FIG. 4 depicts a diagrammatic view illustrating the division of the measuring period into a plurality of intervals in which the numbers of measured counts are assumed to be constant.

In reference to FIG. 4, the unit 34 comprises means for dividing a given measuring period $T_1$ into a plurality $n_t$ of intervals $I_i$ in which each piece of information $\Gamma_{g,i}$, $W_i$ is constant, a means for computing a measured number of counts $n_{le,i}$, $n_{he,i}$ at each energy and an estimated count number $\hat{n}_{le,i}$, $\hat{n}_{he,i}$ in each interval $I_i$ from the or each piece of representative information $\Gamma_{g,i}$, $W_i$. The unit 34 also includes a means for iterative adjustment of the value of each piece of representative information constituting a vector $\underline{x}=[\Gamma_{g,1}, \Gamma_{g,Ng}, W_1, \ldots W_{Nw}]$ with Ng designating the number of intervals for the gas fraction and Nw the number of intervals for W. In an alternative expression, the vector $\underline{x}=[\Gamma_g(1), \Gamma_g(k), W(1), \ldots W(i)]$ corresponding to the different values taken by $\Gamma_g$ and W over the measuring period $T_1$ to minimize a residual, as will be described later.

Figure 3:
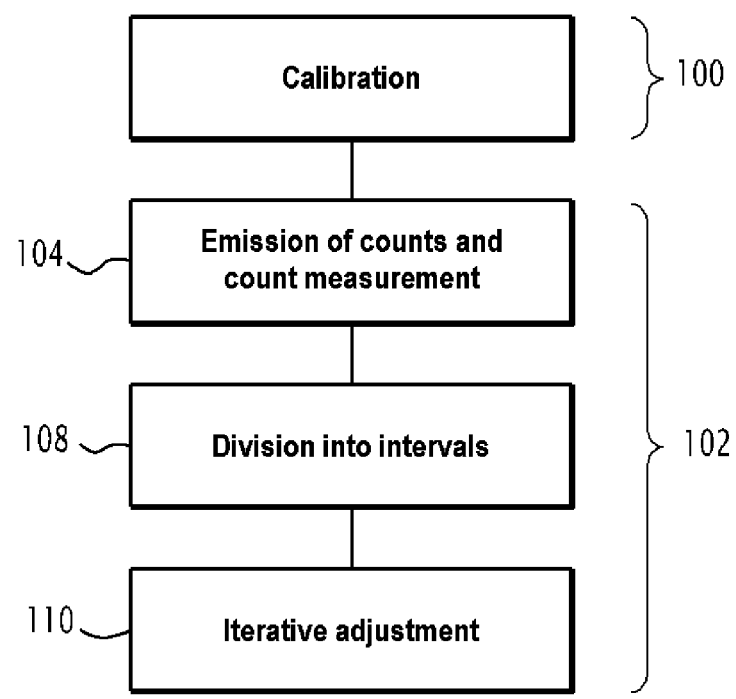
FIG. 3 depicts a functional synoptic diagram illustrating the main phases of the method according to certain embodiments of the present disclosure.

In reference to FIG. 3, a first method for determining representative information $\Gamma_{g,i}$, $W_i$ according to the disclosure includes an initial calibration phase 100 and a measuring phase 102.

The calibration phase 100 includes a step for determining count numbers in an empty pipe measured at each energy $n_{le}^0$, $n_{he}^0$ and a step for determining mass attenuation coefficients, for each phase circulating in the multiphase fluid, at each energy k.

To that end, three monophase samples of gaseous phase, oily liquid phase, and aqueous liquid phase, respectively, are successively arranged in the pipe 14 and are measured. The density $\rho_\phi$ of each phase is also evaluated and the mass attenuation coefficients $\mu_{k,\phi}$ are calculated to deduce the lineic coefficients therefrom using the equation:

$$\lambda_{k,\phi,i} = \rho_{\phi,i} \mu_{k,\phi} \quad (0)$$

The measuring phase 102 includes a step 104 for continuous emission of the beams 36 and 38 at each energy le or he through the fluid 12 and for measuring the gamma photons received by the detector 32 at each measuring moment during the given measuring period $T_1$.

The measuring phase then comprises a step 108 for dividing the measuring period $T_1$ into a plurality of intervals $I(1), \ldots, I(n_t)$ in which each piece of representative information $\Gamma_{g,i}$, $W_i$ will be considered constant. The measuring phase then comprises step 110 for iterative adjustment of the value of each piece of representative information $\Gamma_{g,i}$, $W_i$, for each interval.

Figure 6:
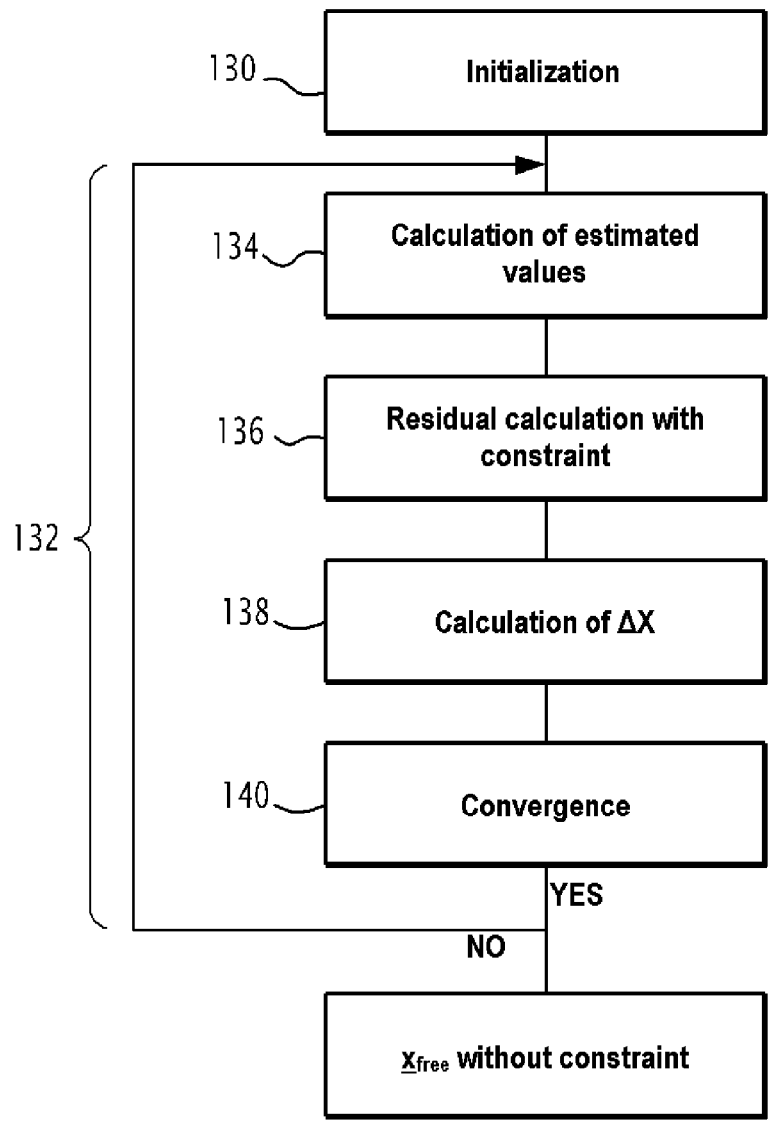
FIG. 6 depicts a functional synoptic diagram illustrating an optimization algorithm with constraints.
Figure 7:
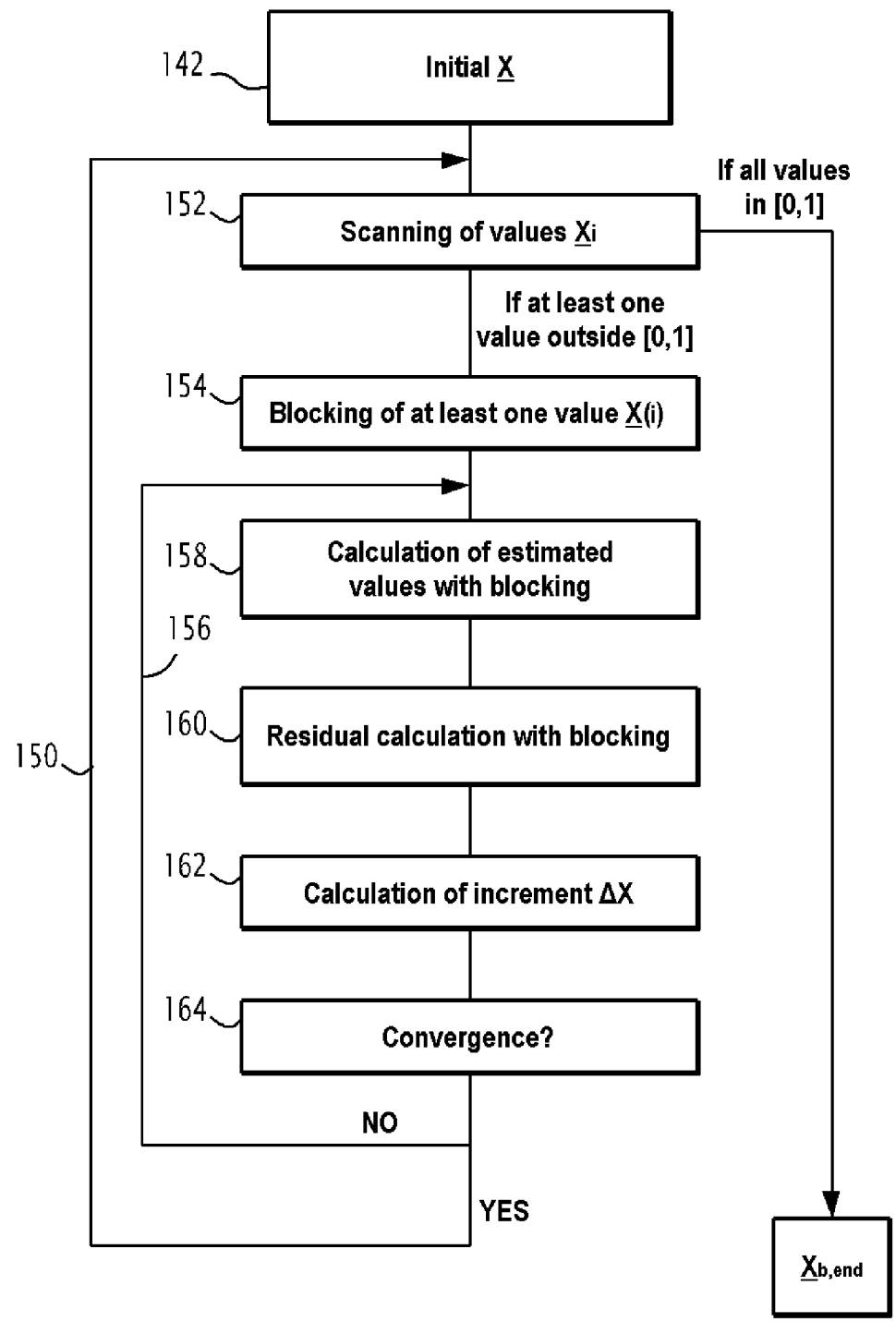
FIG. 7 depicts a view of a synoptic diagram illustrating the implementation of an algorithm for optimizing blocking of the non-physical values.

Step 110 includes, in reference to FIG. 6, a first phase for determining each piece of representative information $\Gamma_{g,i}$, $W_i$ in each interval I by successive iterations until a convergence criteria is verified without blocking of the determined values then, in reference to FIG. 7, a second phase of determining $\Gamma_{g,i}$, $W_i$ through successive iterations by blocking the values coming out of a physical measuring interval of these values and by transferring the corresponding photon counts.

In the measuring step, the photons transmitted through the fluid 12 are collected on the detector 32. A number of photon counts $n_{he,p}$, $n_{le,p}$ of high and low energy, respectively, is collected on the receiver 32 at the measuring pitch p, at an example frequency in the vicinity of 50 Hz.

Figure 5:
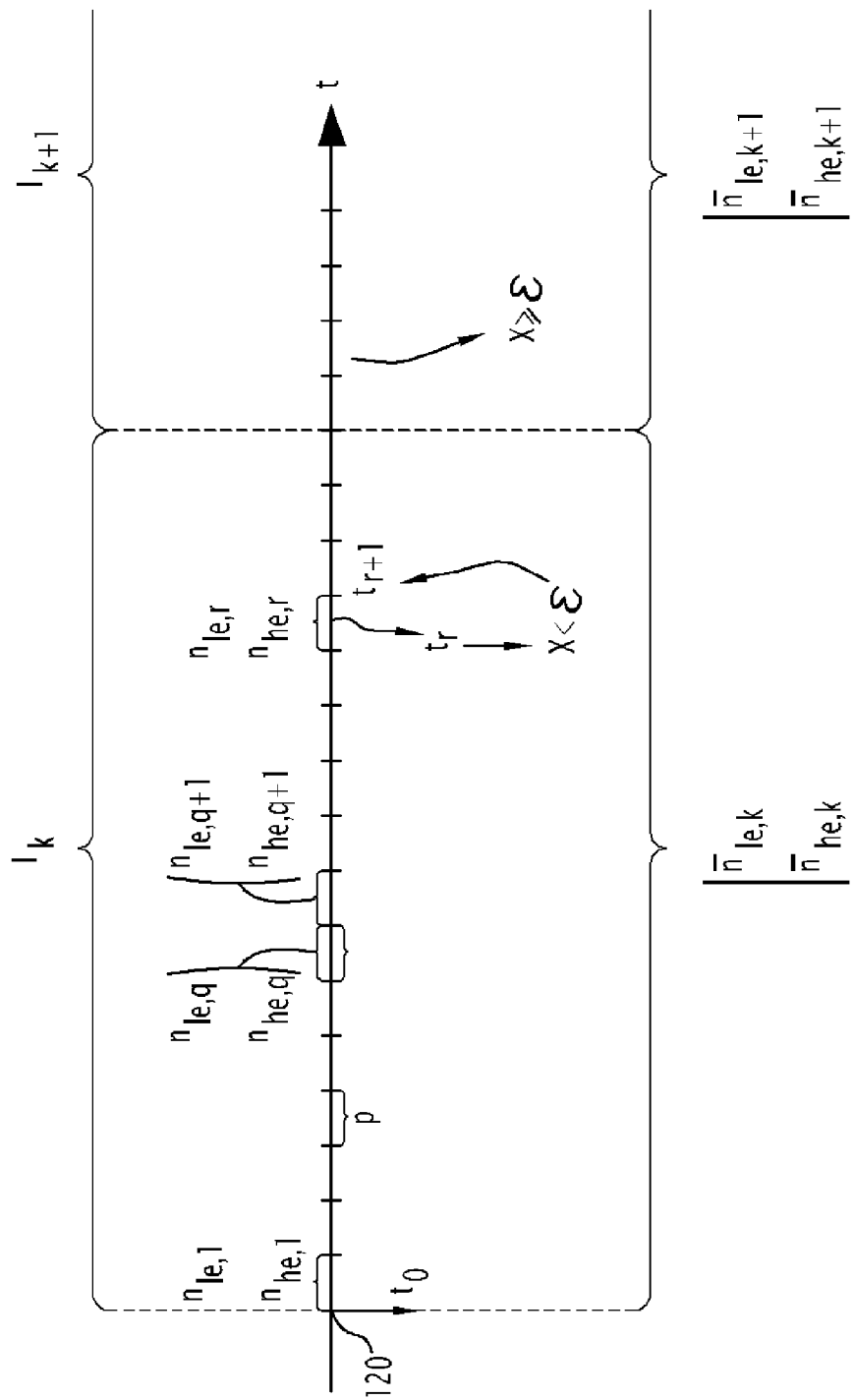
FIG. 5 depicts a diagrammatic view illustrating the principle of the method of dividing the measuring period into a plurality of intervals, in which each measurement is assumed to be constant.

In reference to FIG. 5, in the division step, the beginning 120 of a first measuring interval $I_k$ is defined by measuring the number of counts $n_{he,0}$, $n_{le,0}$ done by the detector 34 at an initial measuring moment $t_0$ shown in FIG. 4.

Then, at each measuring moment $t_r$ after the initial moment $t_0$, the expectation, variance, and covariance of the numbers of measured counts at the pitch p between the initial measuring moment $t_0$ and the measuring moment $t_r$ are calculated, at each energy k, by the formulas:

$$E_k = \frac{1}{N_q} \sum_{q=0}^{r} n_{k,q} \quad (1)$$

$$V_k = \frac{1}{N_q - 1} \sum_{q=0}^{r} (n_{k,q} - E_k)^2 \quad (2)$$

$$C = \frac{1}{N_q - 1} \sum_{q=0}^{r} (n_{le,q} - E_{le}) \cdot (n_{he,q} - E_{he}) \quad (3)$$

where $E_k$, $V_k$ and C are the expectation, variance and covariance, respectively, of the counts measured at energy k, and $n_{k,q}$ is the number of counts of energy k collected at the measuring moment $t_q$, $N_q$ being the number of measuring moments $t_0, \ldots t_r$ between the initial moment $t_0$ and the measuring moment $t_r$.

These statistical magnitudes $V_k$ and C obtained exclusively based on the measured numbers of counts are compared to the theoretical statistical magnitudes obtained by considering a statistical law, advantageously a Poisson law, which would be obtained when the flow is stable, using the following equations:

$$V_k^0 = \frac{E_k}{p} \quad (4)$$

$$C_k^0 = 0 \quad (5)$$

where p is the sampling period separating two consecutive measuring moments.

The deviation between these differences is adimensioned by calculating the standard deviations of the variance and the covariance, assuming that they follow a law of $\chi^2$ by the equations:

$$\sigma_{V_k} = \left(\frac{E_k}{p}\right) \cdot \sqrt{\frac{2}{N_q - 1}} \quad (6)$$

$$\sigma_C = \left(\frac{1}{p}\right) \cdot \sqrt{\frac{E_{le} \cdot E_{he}}{N_q - 1}} \quad (7)$$

Then, an indicator $\chi$ representative of the difference between the measured statistics of the numbers of counts and the theoretical statistics obtained from the Poisson law is calculated using the equation:

$$\chi^2 = \frac{1}{3}\left[\left(\frac{V_{le} - V_{le}^0}{\sigma_{V_{le}}}\right)^2 + \left(\frac{V_{he} - V_{he}^0}{\sigma_{V_{he}}}\right)^2 + \left(\frac{C}{\sigma_C}\right)^2\right] \quad (8)$$

If this indicator $\chi$ is below a predetermined value $\epsilon$, for example equal to 1, the flow is still considered stable, and the preceding steps are repeated considering the numbers of counts between the initial measuring moment and the measuring moment $t_{r+1}$ following the moment $t_r$.

If this indicator $\chi$ is above a predetermined value $\epsilon$, the flow is considered unstable.

The measuring moment $t_r$ then constitutes the beginning of a second measuring interval $I_{k+1}$ that is determined iteratively, as described for the first interval $I_k$.

As illustrated by FIG. 4, it is thus possible to determine the different intervals $I_{\Gamma 1}, \ldots, I_{\Gamma k}$ for which the flow is considered stable. In each interval $I_{\Gamma 1}, \ldots, I_{\Gamma k}$, the first piece of representative information $\Gamma_{g,i}$ is considered constant.

Likewise, a plurality of intervals $I_{W1}, \ldots, I_{WT}$ in which the second piece of representative information $W_i$ is considered constant is determined by a calculation or is fixed empirically.

Once the intervals $I_{\Gamma 1}, \ldots, I_{\Gamma k}$, and $I_{W1}, \ldots, I_{WT}$ are set for each of the pieces of representative information $\Gamma_{g,i}$ and $W_i$, the measuring period $T_1$ is divided into a plurality of intervals $I_1, \ldots, I_{nt}$ so that in each interval $I_1, \ldots, I_{nt}$, each piece of representative information $\Gamma_{g,i}$ and $W_i$ is assumed to be constant.

As illustrated by FIG. 4, tables $\underline{Z}_\Gamma$ and $\underline{Z}_W$ connecting each of the intervals $I_1, \ldots, I_{nt}$ and the values $\Gamma_{g,i}$ and $W_i$ on which they depend are built.

Moreover, for each energy k, the number of counts $n_k(i)$ measured by the detector 32 in each interval $I_i$ among the intervals $I_1, \ldots, I_{nt}$ is calculated by averaging the number of counts $n_{k,q}$ measured at each measuring moment $t_r$ in the interval $I_i$.

The duration $\Delta t_i$ of each interval $I_i$ is therefore variable and is stored in a vector $\underline{\Delta t_i}$. Likewise, the values of the numbers of counts $n_{le,i}$, $n_{he,i}$ measured at high energy and low energy, respectively, in each interval i are stored in a matrix $\underline{n}$ with dimensions $n_t \times 2$.

Lineic attenuation coefficients $\lambda_{g,k,i}$; $\lambda_{o,k,i}$; $\lambda_{w,k,i}$ are calculated for each phase and for each energy k in each interval $I_i$, based on the coefficients $\mu_{k,\phi}$ and densities $\rho_\phi$ and are stored in a matrix $\underline{\Lambda}$ with dimensions $n_t \times 6$.

Then, in reference to FIG. 6, a step for determining each piece of representative information $\Gamma_{g,i}$ and $W_i$ in each interval $I_{\Gamma 1}, \ldots, I_{\Gamma k}$, and $I_{W 1}, \ldots, I_{WT}$ is done by successive iterations until a convergence criterion is verified, without blocking of the obtained values of $\Gamma_{g,i}$ and $W_i$.

To that end, in the initialization step 130, a vector $\underline{x}_{init} = [\Gamma_{g,i}(init), \ldots, \Gamma_{g,k}(init), W_1(init), \ldots W_T(init)]$ is initially defined.

Then, a series of iterations m, designated by reference 132, is done to determine the value of the vector $\underline{x}_{free} = [\Gamma_{g,i}(free), \Gamma_{g,k}(free), W_0(free), W_T(free)]$ in each interval $I_{\Gamma 1}, \ldots, I_{\Gamma k}$, and $I_{W 1}, \ldots, I_{WT}$ when a convergence is obtained without blocking the values.

Each iteration 132 comprises the calculation 134 for each interval $I_1, \ldots, I_{nt}$ of the estimated numbers of counts measured at high energy and low energy $\hat{n}_{le,i}, \hat{n}_{he,i}$ based on the first information $\Gamma_{g,i}(m)$, $W_i(m)$ obtained in the preceding iteration and a Beer-Lambert law, using the equation:

$$\hat{n}_{k,i} = n_k^0 \cdot \exp\left(-d \cdot \sum_{\varphi=g,w,o} \lambda_{k,\varphi,i} \Gamma_{g,i}(m)\right) = n_k^0 \cdot \exp(-d \cdot \lambda_{k,i}) \quad (9)$$

where d is the diameter of the pipe, $\lambda_{k,\varphi,i}$ is the lineic attenuation coefficient of the phase at energy k during the interval $I_i$.

Likewise, each iteration m comprises the calculation for each interval $I_1, \ldots, I_{nt}$ of the estimated numbers of counts in an empty pipe $\hat{n}_{le,i}^0, \hat{n}_{he,i}^0$ at high energy and low energy for each measuring interval i based on first information $\Gamma_{g,i}(m)$, $W_i(m)$ obtained in the preceding iteration and from a Beer-Lambert law, using the equation:

$$\hat{n}_{k,i}^0 = n_{k,i} \cdot \exp\left(+d \cdot \sum_{\varphi=g,w,o} \lambda_{k,\varphi,i} \Gamma_{g,i}(m)\right) = n_{k,i} \cdot \exp(+d \cdot \lambda_{k,i}) \quad (10)$$

For each measuring interval $I_I$ between $I_1$ and $I_{nt}$, the values of $\Gamma_{g,i}(m)$ and $W_i(m)$ are extracted from the vector $\underline{x}(m)$ using correspondence tables $\underline{Z}_\Gamma$ and $\underline{Z}_W$.

Then the aqueous and oily phase fractions are calculated using the equations $$\Gamma_{w,i} = (1 - \Gamma_{g,i}) \cdot W_i \quad (11)$$

$$\Gamma_{o,i} = (1 - \Gamma_{g,i}) \cdot (1 - W_i) \quad (12)$$

Then, the global lineic attenuation coefficients are calculated for each interval $I_i$ at each energy using the equations:

$$\lambda_{le,i} = \underline{\Lambda}(i,1) \cdot \Gamma_{g,i} + \underline{\Lambda}(i,2) \cdot \Gamma_{w,i} + \underline{\Lambda}(i,3) \cdot \Gamma_{o,i} \quad (13)$$

$$\lambda_{he,i} = \underline{\Lambda}(i,4) \cdot \Gamma_{g,i} + \underline{\Lambda}(i,5) \cdot \Gamma_{w,i} + \underline{\Lambda}(i,6) \cdot \Gamma_{o,i} \quad (13)$$

This being done, the estimated numbers of measured counts $\hat{n}_{le,i}, \hat{n}_{he,i}$ bet at low energy and high energy, respectively, are calculated using equation (9) above for each interval $I_i$ and vectors $\hat{n}_{le}, \hat{n}_{he}$ with dimensions $n_t$ are obtained.

Likewise, the estimated numbers of counts in an empty pipe $\hat{n}_{le,i}^0, \hat{n}_{he,i}^0$ at high energy and low energy for each measuring interval $I_i$ are calculated based on equation (10) above and vectors $\hat{n}_{le}^0, \hat{n}_{he}^0$ with dimension $n_t$ are obtained.

Then, in step 136, a residual L0 is determined as a function of a first criterion $C_1$ calculated from probabilities $P1_{k,i} = P[n_{k,1}|\hat{n}_{k,i}(\underline{x})]$, according to a given statistical law, to measure, for each energy, the number of measured counts $n_{le,i}, n_{he,i}$ at each interval $I_i$, the given statistical law being parameterized based on the number of estimated counts $\hat{n}_{le,i}, \hat{n}_{he,i}$ at each interval, based on the values $\Gamma_{g,i}$ and $W_i$ in each interval.

Advantageously, the statistical law is a Poisson law.

To do this, the first criterion $C_1$ is obtained by computing, for each energy, the probability $P1_{k,i}$ at each moment i using the following formula:

$$P1_{k,i} = \frac{\exp(-\hat{N}1) \times (\hat{N}1)^{N1}}{\Gamma(N1+1)} \quad (15)$$

$\Gamma$ being the gamma function, where N1 is obtained by making the scalar product of the vectors $\underline{n}_k$ and $\underline{\Delta t}_i$ and $\hat{N}1$ obtained by making the scalar product of vectors $\hat{\underline{n}}_k$ and $\underline{\Delta t}_i$.

Then, the first criterion $C_1$ is calculated using the equation:

$$C_1 = f_{le} + f_{he} = \sum_{k=le,he} -\sum_{i=1}^{n_t} \log\{P[n_{k,i}|\hat{n}_{k,i}(x)]\} = \sum_{k=le,he} -\sum_{i=1}^{n_t} \log P1_{k,i} \quad (16)$$

In this calculation of a maximum likelihood, it is equivalent to making the product of the probabilities $P1_{k,i}$ or minimizing the sum of the terms $-\log P1_{k,i}$.

According to the present disclosure, the residual L0 also comprises a second criterion $C_2$ that is calculated from probabilities using a given statistical law to measure, for each energy, an average number of counts, the given statistical law being parameterized based on the average of the same estimated number of counts for each interval $I_i$, based on the values $\Gamma_{g,i}$ and $W_i$ in each interval.

The average number of counts is advantageously the number $n_k^0$ of counts in an empty pipe measured during the calibration step for each energy k. The number of estimated counts for each interval $I_i$ is given by the calculation of $\hat{n}_{le,i}^0, \hat{n}_{he,i}^0$ using equation (10).

To calculate the second criterion $C_2$, the average $\hat{E}_k^0$ of the number of counts in an empty pipe estimated for each energy k is calculated based on the following equation:

$$\hat{E}_k^0 = \left(\frac{1}{T}\right) \cdot \left(\sum_{i=1}^{nt} \hat{n}_{k,i}^0 \cdot \Delta t_i\right) \quad (17)$$

$$\text{where } T = \left(\sum_{i=1}^{nt} \Delta t_i\right) \quad (18)$$

Then, for each energy, the probability $$P2_k = P\left[n_k^0 \mid \hat{n}_{k,i}^0(x)\right]$$

of measuring $n_k^0$ numbers of counts in an empty pipe at energy k is calculated, according to a given statistical law knowing that the value of the average is estimated at $\hat{E}_k^0$, the average $\hat{E}_k^0$ being calculated based on the representative information $\Gamma_{g,i}$ and $W_i$ using equations (10) to (14) above.

The statistical law is advantageously the Poisson Law. The probability P2 is then calculated using the equation:

$$P2_k = \frac{\exp(-\hat{N}2) \times (\hat{N}2)^{N2}}{\Gamma(N2+1)} \quad (19)$$

$$\text{where } N2 = n_k^0 \times T \text{ and } \hat{N}2 = \hat{E}_k^0 \times T \quad (20)$$

The second criterion $C_2$ is the calculated using the equation:

$$C2 = \quad (21)$$
$$\omega \cdot (m_{le} + m_{he}) = \omega \cdot \left[\sum_{le,he} -\log(P2_k)\right] = \omega \cdot \left[\sum_{le,he} -\log\left(P\left[n_k^0 \mid \overline{\hat{n}_{k,i}^0}(x)\right]\right)\right]$$

where $\omega$ is a weight coefficient, for example equal to the square of $n_t$.

Then, the residual L0 is calculated using the following formula:

$$L0 = C_1 + C_2 = f_{le} + f_{he} + \omega \cdot (m_{le} + m_{he}) \quad (22)$$

In the following step 138 of the iteration m, a vectoral increment $\Delta \underline{x}$ is calculated to come closer to the convergence by causing a decrease of the residual L1, to reach a maximum likelihood between, on one hand, the measured values $n_{k,i}$, and the estimated values $$\hat{n}_{k,i},$$

and between, on the other hand, the average value $n_k^0$ and the average of the estimated values $$\overline{\hat{n}_{k,i}^0}(x).$$

The increment $\Delta \underline{x}$ can be calculated by a variety of numerical methods. In this example, the Newton method can be used by calculating the Hessian matrix (second derivative) $\underline{H}$ and the gradient g (first derivative) of the residual L1 at the point under consideration $\underline{x}$.

The matrix system $\underline{H} \cdot \Delta \underline{x} = -g$ is then resolved.

In practice, it is possible to simplify the Poisson law of probability with a normal law and to calculate the residual using the Gauss-Newton method. These methods are known by those skilled in the art.

Once the increment is calculated, a new value of each piece of representative information $\Gamma_{g,i}$ (m+1) and $W_i$(m+1) is obtained using the formula:

$$\underline{x}(m+1) = [\Gamma_{g,1}(m+1), \ldots, \Gamma_{g,k}(m+1), W_1(m+1), \ldots, W_i(m+1)] = \underline{x}(m) + \Delta \underline{x} \quad (23)$$

The iterations m are repeated until a convergence criterion is verified in step 140.

In this example, the convergence criterion is for example calculated by the maximum absolute value Vmax of each term of the increment $\Delta \underline{x}$. If Vmax is greater than a given value, for example less than $10^{-6}$, a new iteration m is done, while if Vmax is less than $\epsilon$, the convergence criterion is met.

Alternatively, the convergence criterion can be determined by a stop criterion on the gradient. In step 142, when the convergence criterion is met, the matrix $\underline{x}_{free} = [\Gamma_{g,1}(\text{free}), \ldots, \Gamma_{g,k}(\text{free}), W_0(\text{free}), \ldots W_1(\text{free})]$ is obtained.

In reference to FIG. 7, this matrix is processed so that each value $\Gamma_{g,i}$, $W_i$ is included in an interval of possible physical measurements [a, b], which in this example is between 0 and 1.

To that end, a series of iterations 150 is done, as long as there is still a value of $\underline{x}_i$ situated outside the interval of physical measurements [a, b].

Upon each iteration 150, each value $\underline{x}_i$ is scanned in step 152 to verify whether that value is below the minimum boundary a of the interval of physical measurements or is greater than the maximum boundary b of the interval of physical measurements.

In a first alternative, all of the values of $\underline{x}_i$ of the vector $\underline{x}$ of the representative information $\Gamma_{g,i}$ and $W_i$ that exceed a boundary a, b of the physical measurement interval are attributed the value $x_L$=a or b of the boundary, and all of the variables $x_L$ are blocked at that value $x_L$, so that they keep that value until the convergence.

In a second alternative, a first group of values $\underline{x}_i$ exceeding a boundary a, b of the physical measurement interval is assigned the value $x_L$ of the corresponding boundary, and all of the variables of the first group are blocked at the value $X_L$ until the convergence. On the contrary, a second group of values $\underline{x}_i$ exceeding a boundary a, b are kept at their initial values and these variables are left free during different iterations.

Thus, in one example, the value $\underline{x}_i$ exceeding a boundary, creating the greatest transfer of counts, is determined. This value $x_i$ is then set at the value $x_L$ of the boundary and is blocked until the convergence.

The count transfer resulting from the blockage of the variable $\underline{x}_i$ is determined.

To that end, a first residual L1 is calculated for the vector $\underline{x}_{free}$ obtained before blockage of the variable $\underline{x}_i$ using equation (22) above.

Then, a second residual L2 is calculated using equation (22) based on the vector $x_b$ equal to $\underline{x}$ with the exception of the variable $x_{b,i}$, which was blocked at the value $x_L$.

The absolute value $\Delta L = |L2 - L1|$ of the difference between the residuals L1 and L2 is then evaluated for each value $\underline{x}_i$ exceeding a boundary a, b and the value creating the most count transfers, i.e. the biggest $\Delta L$, is kept constant for the continuation at the value $x_L$.

A new vector $\underline{x}_b$ with at least one blocked value is then defined in step 154. The vector $\underline{x}_b$ is then adjusted by iterations 156 to reach a maximum likelihood with the vector $\underline{x}_{free}$ obtained at the end of the optimization without blockage in step 142.

This adjustment is done using the calculation, in step 160, of a residual with blockage L3 comprising the second criterion $C_2$ defined in equation (21). The residual L3 also includes a third criterion $C_3$ calculated from the probabilities $P3_{k,i} = P[\hat{n}_{k,i}(\underline{x}_{free}) | \hat{n}_{k,i}(\underline{x}_b)]$, according to a given statistical law, to measure, for each energy k and in each interval $I_i$, the number of estimated counts $\hat{n}_{k,i}(\underline{x}_{free})$ for the vector $\underline{x}_{free}$ obtained by the optimization without blocking, the given statistical law being parameterized based on the number of estimated counts $\hat{n}_{k,i}(\underline{x}_b)$ for the vector blocked at each interval during each iteration 150.

The third criterion C3 is calculated using the following equation:

$$C3 = \sum_{le,he} g_k(\underline{x}_{free}, \underline{x}_b) = \sum_{le,he}\left(-\sum_{i=1}^{nt} \omega'_{k,i} \log(P[\hat{n}_{k,i}(\underline{x}_{free}) | \hat{n}_{k,i}(\underline{x}_b)])\right)$$

where $\omega'_{k,i}$ is a weight calculated from the probability of the count transfer resulting from blocking at least one variable of the vector $\underline{x}_b$.

The probability $P3_{k,i} = P[\hat{n}_{k,i}(\underline{x}_{free}) | \hat{n}_{k,i}(\underline{x}_b)]$ is calculated based on the Poisson law as described above.

To calculate the weight $\omega'_{k,i}$ resulting from blocking the variable $x_L$, one determines whether the variable $x_L$ constitutes a first piece of representative information $\Gamma_{g,i}$, or a second piece of representative information $W_i$.

In the first case, a vector $\underline{x}_{ref}$ is built by blocking all of the values of $\Gamma_{g,i}$ at the blocked value $x_L$. In the second case, the vector $\underline{x}_{ref}$ is built by blocking all of the values of $W_i$ at the blocked value $x_L$.

Then, in step 158, the estimated count numbers $\hat{n}_{k,i}(\underline{x}_{ref})$ are calculated based on the vector $\underline{x}_{ref}$ at each moment $I_i$ for each energy k using equations (9) and (11) to (14).

Then, the coefficients $\omega'_{k,i}$ are calculated by determining the probability $P4_{k,i} = P[\hat{n}_{k,i}(\underline{x}_{free}) | \hat{n}_{k,i}(\underline{x}_b)]$ using the Poisson Law as previously described, using the equation:

$$P4_{k,i} = \frac{\exp(-\hat{N}4) \times (\hat{N}4)^{N4}}{\Gamma(N4+1)} \quad (25)$$

where N4 is obtained by making the scalar product of the vectors $\underline{\hat{n}}_{k,i}(\underline{x}_{ref})$ and $\underline{\Delta t}_i$ and $\hat{N}4$ is obtained by making the scalar product of the vectors $\underline{\hat{n}}_k(\underline{x}_b)$ and $\underline{\Delta t}_i$.

Then, $\omega'_{k,i}$ is calculated using the equation:

$$\omega'_{k,i} = (P3_{k,i})^{\frac{1}{2}} \quad (26)$$

The residual L3 is calculated using the equation:

$$L3 = C_2 + C_3 \quad (27)$$

Then, in step 162, an increment $\Delta\underline{x}$ is calculated to decrease the residual L3, as previously described in step 138, to reach a maximum likelihood between, on one hand, the estimated values $\hat{n}_{k,i}(\underline{x}_{free})$ obtained without blocking, and the estimated values $\hat{n}_{k,i}(\underline{x}_b)$ obtained after blocking, and between, on the other hand, the average value $n_k^0$ and the average of the estimated values $$\overline{\hat{n}_{k,i}^0(\underline{x})}.$$

The iterations are repeated as long as the convergence criterion of step 164 has not been met.

This criterion is advantageously equal to the criterion defined in step 140.

Once the convergence criterion is met, and once all of the values $x_{b,i}$ of the vector $\underline{x}_b$ obtained after blocking are included in the interval [a, b] of physical values, the vector $\underline{x}_b$ end obtained describes all of the values $\Gamma_{g,i}$ and $W_i$ on the different measuring intervals of the measuring period $T_1$. Another measuring period can then be processed.

In the disclosure hereof, the optimization done by using the second criterion $C_2$ significantly improves the precision of the results obtained on the calculation of the representative information $\Gamma_{g,i}$ and $W_i$, in particular when the gas content is high.

Blocking physically incorrect values of $\Gamma_{g,i}$ and $W_i$ and the weighted transfer of the count numbers having led to those values makes it possible to offset the errors naturally observed, without introducing a significant statistical bias.

It is thus possible to obtain great precision while also keeping excellent measurement dynamics.

The methods used are numerically easy to resolve and more reliable than using a direct resolution method.

Dividing the measuring period $T_1$ into a plurality of intervals $I_i$ using an adaptive method greatly simplifies the numerical resolution of the problem posed by limiting the number of statistical values with a minimal risk of not capturing variations of the flow.

The division method is based solely on the statistics of the number of measured counts, which makes it particularly simple to carry out.

The invention claimed is:

1. A method for determining at least one piece of information ($\Gamma_g$, W) representative of a phase fraction of a multiphase fluid circulating in a pipe, the method comprising the steps of:
    (a) emitting a number of gamma photon counts at at least one energy through the fluid, and
    (b) measuring a number of counts ($n_{le}$, $n_{he}$) received for each energy, after passage in the fluid;
    (c) dividing a given measuring period ($T_1$) into a plurality of measuring intervals ($I_i$) in which each piece of representative information ($\Gamma_{g,i}$, $W_i$) is assumed to be constant;
    (d) choosing an initial value of the or each piece of representative information ($\Gamma_{g,i}$, $W_i$) in each interval;
    (e) determining the or each piece of representative information ($\Gamma_{g,i}$, $W_i$) in each interval ($I_i$) through successive iterations until a convergence criterion is verified, each iteration comprising:
    ($e_1$) estimating a number of counts received ($\hat{n}_{le,i}$, $\hat{n}_{he,i}$) at each energy in each interval ($I_i$) based on the or each piece of representative information ($\Gamma_{g,i}$, $W_i$) determined at a preceding iteration,
    ($e_2$) calculating a residual ($L_0$) comprising a first criterion ($C_1$) calculated from probabilities according to a given statistical law to measure, for each energy, the number of counts ($n_{le,i}$, $n_{he,i}$) measured at each interval, the given statistical law being parameterized based on the number of counts estimated ($\hat{n}_{le,i}$, $\hat{n}_{he,i}$) in step ($e_1$) at each interval ($I_i$);
    ($e_3$) determining new values of the or each piece of representative information ($\Gamma_{g,i}$, $W_i$) to minimize the residual ($L_0$);
    step (e) including, at each iteration,
    ($e_4$) calculating the average ($\hat{E}_k^0$), for each energy, of an estimated number of counts ($\hat{n}_k^0$) for each interval ($I_i$) based on the representative information ($\Gamma_{g,i}$, $W_i$) determined in a preceding iteration, the residual ($L_0$) calculated in step ($e_2$) comprising a second criterion ($C_2$) calculated from probabilities according to a given statistical law to measure, for each energy, an average number of counts ($n_k^0$), the given statistical law being parameterized based on the average ($\hat{E}_k^0$) calculated in step ($e_4$).

2. The method according to claim 1, wherein for each energy, the average count number is an average number of counts in an empty pipe ($n_k^0$) measured during a calibration step at each energy, in the absence of fluid in the pipe, the step ($e_4$) including the calculation of the average ($\hat{E}_k^0$) for each energy, of the number of counts in an empty pipe ($\hat{n}_k^0$) estimated for each interval based on the representative information ($\Gamma_{g,i}$, $W_i$) determined in a preceding iteration.

3. The method according to claim 1, wherein the representative information ($\Gamma_{g,i}$, $W_i$) is respectively the lineic fraction of gas ($\Gamma_{g,i}$) according to a diameter of the pipe and the volume fraction of water ($W_i$) in the liquid phase present in the multiphase fluid.

4. The method according to claim 1, wherein the statistical law is a Poisson law.

5. The method according to claim 1, wherein the residual (L) is calculated using the formula:

$$f_{le}+f_{he}+\omega \cdot (m_{le}+m_{he})$$

in which $f_{le}$ and $f_{he}$ are the first criteria ($C_1$) calculated at a first energy and a second energy, respectively, $m_{le}$ and $m_{he}$ are the second criteria ($C_2$) calculated at the first energy and the second energy, respectively, and $\omega$ is a weight coefficient.

6. The method of claim 1, further comprising scanning the raw representative information ($\Gamma_{g,i}$(free), $W_i$(free)) obtained at the end of step (e) at each interval ($I_i$) to determine the raw representative information coming from a given interval of physical values ([a, b]), then blocking at least one piece of raw representative information ($x_i$) coming out of the interval of physical values so that its value ($x_L$) remains equal to one end of the interval, the method then comprising a step (f) for determining each piece of representative information ($\Gamma_{g,i}$, $W_i$) in each interval through successive iterations until verification of a convergence criterion, each iteration comprising:

($f_1$) estimating a number of counts ($\hat{n}_{k,i}(\underline{x}_b)$) received at each energy in each interval based on the representative information determined at a preceding iteration from representative information obtained after blocking the or each piece of locked representative information;

($f_2$) calculating a residual ($L_3$) comprising a third criterion ($C_3$) calculated from probabilities according to a given statistical law to measure, for each energy, the number of estimated counts ($\hat{n}_{k,i}(\underline{x}_{free})$) at each interval from representative information obtained without blocking at the end of step (e), the given statistical law being parameterized based on the number of counts $\hat{n}_{k,i}(\underline{x}_b)$ estimated in step ($f_1$) at each interval.

7. The method according to claim 6, wherein the blocking step includes the selection of at least a first group of representative information ($\Gamma_{g,i}$, $W_i$) having a value situated outside the interval of physical values given, without locking a second group of determined representative information having a value situated outside the interval of given physical values, then carrying out step (f).

8. The method according to claim 6, wherein the or each piece of blocked representative information is chosen based on a criterion ($\Delta L$) representative of the count transfer resulting from locking the representative information.

9. The method according to claim 6, wherein the step of calculating the third criterion ($C_3$) comprises calculating a count transfer probability coefficient [$\omega'_{k,i}$] resulting from blocking at least one piece of representative information in each interval at each energy to weight each probability calculated in step ($f_2$).

10. The method according to claim 1, wherein the step for dividing the given period into a plurality of intervals comprises:

($c_1$) for each interval, determining a beginning of an interval ($t_0$), then calculating, for successive measuring moments ($t_r$) moving away from the beginning of the interval ($t_0$), at least one difference between at least one statistical magnitude ($V_k$, C) calculated from the number of counts measured between the beginning of the interval ($t_0$) and the measuring moment ($t_r$) after the beginning of the interval ($t_0$) and the same statistical magnitude ($V_k^0$, $C^0$) calculated based on a known statistical law, until a criterion determined based on said difference is greater than a determined value, the measuring moment in progress then constituting the beginning of another interval, ($c_2$) calculating the average of the number of counts ($n_{k,q}$) measured at each energy at each measuring moment ($t_r$) in the interval, the average of the number of measured counts defining the number of counts ($n_{k,i}$) measured in the interval;

($c_3$) repeating steps ($c_1$) and ($c_2$) to define the other interval from the moment following the end of the interval.

11. The method according to claim 10, wherein the statistical magnitude comprises the variance ($V_k$) and/or covariance (C) of the number of counts ($n_{k,q}$) measured at each measuring moment between the beginning of the interval and the subsequent measuring moment.

12. The method of claim 10, wherein the statistical law is a Poisson law, the statistical magnitude being calculated from the Poisson law.

13. The method according to claim 12, wherein the step of determining the criterion comprises calculating at least the difference $$\left[\frac{V_k - V_k^0}{\sigma_{V_k}}\right],$$

where k is the energy, $V_k$ is the variance of the number of measured counts between the beginning of the interval and the measuring moment ($t_r$) after the beginning of the interval, $V_k^0$ is the variance calculated from the statistical law, and $\sigma_{V_k}$ is the standard deviation calculated from the statistical law.

14. A method for determining at least one piece of information ($\Gamma_g$, W) representative of a phase fraction of a multiphase fluid circulating in a pipe, the method comprising the steps of:

(f) emitting a number of gamma photon counts at least one energy through the fluid, and (g) measuring a number of counts ($n_{le}$, $n_{he}$) received for each energy, after passage in the fluid;

(h) dividing a given measuring period ($T_1$) into a plurality of measuring intervals ($I_i$) in which each piece of representative information ($\Gamma_{g,i}$, $W_i$) is assumed to be constant;

(i) choosing an initial value of the or each piece of representative information ($\Gamma_{g,i}$, $W_i$) in each interval;

(j) determining the or each piece of representative information ($\Gamma_{g,i}$, $W_i$) in each interval ($I_i$) through successive iterations until a convergence criterion is verified, each iteration comprising:

($e_1$) estimating a number of counts received ($\hat{n}_{le,i}$, $\hat{n}_{he,i}$) at each energy in each interval ($I_i$) based on the or each piece of representative information ($\Gamma_{g,i}$, $W_i$) determined at a preceding iteration, ($e_2$) calculating a residual ($L_0$) comprising a first criterion ($C_1$) calculated from probabilities according to a given statistical law to measure, for each energy, the number of counts ($n_{le,i}$, $n_{he,i}$) measured at each interval, the given statistical law being parameterized based on the number of counts estimated ($\hat{n}_{le,i}$, $\hat{n}_{he,i}$) in step ($e_1$) at each interval ($I_i$);

($e_3$) determining new values of the or each piece of representative information ($\Gamma_{g,i}$, $W_i$) to minimize the residual ($L_0$);

step (e) including, at each iteration, ($e_4$) calculating the average ($\hat{E}_k^0$), for each energy, of an estimated number of counts ($\hat{n}_k^0$) for each interval ($I_i$) based on the representative information ($\Gamma_{g,i}$, $W_i$) determined in a preceding iteration, the residual ($L_0$) calculated in step ($e_2$) comprising a second criterion ($C_2$) calculated from probabilities according to a given statistical law to measure, for each energy, an average number of counts ($n_k^0$) the given statistical law being parameterized based on the average ($\hat{E}_k^0$) calculated in step ($e_4$);

and further comprising scanning the raw representative information ($\Gamma_{g,i}$(free), $W_i$(free)) obtained at the end of step (e) at each interval ($I_i$) to determine the raw representative information coming from a given interval of physical values ([a, b]), then blocking at least one piece of raw representative information ($x_i$) coming out of the interval of physical values so that its value ($x_L$) remains equal to one end of the interval, the method then comprising a step (f) for determining each piece of representative information ($\Gamma_{g,i}$, $W_i$) in each interval through successive iterations until verification of a convergence criterion, each iteration comprising:

($f_1$) estimating a number of counts ($\hat{n}_{k,i}(\underline{x}_b)$) received at each energy in each interval based on the representative information determined at a preceding iteration from representative information obtained after blocking the or each piece of locked representative information;

($f_2$) calculating a residual ($L_3$) comprising a third criterion ($C_3$) calculated from probabilities according to a given statistical law to measure, for each energy, the number of estimated counts ($\hat{n}_{k,i}(\underline{x}_{free})$) at each interval from representative information obtained without blocking at the end of step (e), the given statistical law being parameterized based on the number of counts $\hat{n}_{k,i}(\underline{x}_b)$ estimated in step ($f_1$) at each interval.

15. The method according to claim 14, wherein the blocking step includes the selection of at least a first group of representative information ($\Gamma_{g,i}$, $W_i$) having a value situated outside the interval of physical values given, without locking a second group of determined representative information having a value situated outside the interval of given physical values, then carrying out step (f).

16. The method according to claim 14, wherein the or each piece of blocked representative information is chosen based on a criterion ($\Delta L$) representative of the count transfer resulting from locking the representative information.

17. The method according to claim 14, wherein the step of calculating the third criterion ($C_3$) comprises calculating a count transfer probability coefficient [$\omega'_{k,i}$] resulting from blocking at least one piece of representative information in each interval at each energy to weight each probability calculated in step ($f_2$).

18. The method according to claim 14, wherein the step for dividing the given period into a plurality of intervals comprises:

($c_1$) for each interval, determining a beginning of an interval ($t_0$), then calculating, for successive measuring moments ($t_r$) moving away from the beginning of the interval ($t_0$), at least one difference between at least one statistical magnitude ($V_k$, C) calculated from the number of counts measured between the beginning of the interval ($t_0$) and the measuring moment ($t_r$) after the beginning of the interval ($t_0$) and the same statistical magnitude ($V_k^0$, $C^0$) calculated based on a known statistical law, until a criterion determined based on said difference is greater than a determined value, the measuring moment in progress then constituting the beginning of another interval, ($c_2$) calculating the average of the number of counts ($n_{k,q}$) measured at each energy at each measuring moment ($t_r$) in the interval, the average of the number of measured counts defining the number of counts ($n_{k,i}$) measured in the interval;

($c_3$) repeating steps ($c_1$) and ($c_2$) to define the other interval from the moment following the end of the interval.

19. The method according to claim 18, wherein the statistical magnitude comprises the variance ($V_k$) and/or covariance (C) of the number of counts ($n_{k,q}$) measured at each measuring moment between the beginning of the interval and the subsequent measuring moment.

20. The method of claim 18, wherein the statistical law is a Poisson law, the statistical magnitude being calculated from the Poisson law.

21. A method for determining at least one piece of information ($\Gamma_g$, W) representative of a phase fraction of a multiphase fluid circulating in a pipe, the method comprising the steps of:

(k) emitting a number of gamma photon counts at least one energy through the fluid, and (l) measuring a number of counts ($n_{le}$, $n_{he}$) received for each energy, after passage in the fluid;

(m) dividing a given measuring period ($T_1$) into a plurality of measuring intervals ($I_i$) in which each piece of representative information ($\Gamma_{g,i}$, $W_i$) is assumed to be constant;

(n) choosing an initial value of the or each piece of representative information ($\Gamma_{g,i}$, $W_i$) in each interval;

(o) determining the or each piece of representative information ($\Gamma_{g,i}$, $W_i$) in each interval ($I_i$) through successive iterations until a convergence criterion is verified, each iteration comprising:

($e_1$) estimating a number of counts received ($\hat{n}_{le,i}$, $\hat{n}_{he,i}$) at each energy in each interval ($I_i$) based on the or each piece of representative information ($\Gamma_{g,i}$, $W_i$) determined at a preceding iteration, ($e_2$) calculating a residual ($L_0$) comprising a first criterion ($C_1$) calculated from probabilities according to Poisson law to measure, for each energy, the number of counts ($n_{le,i}$, $n_{he,i}$) measured at each interval, the Poisson law being parameterized based on the number of counts estimated ($\hat{n}_{le,i}$, $\hat{n}_{he,i}$) in step ($e_1$) at each interval ($I_i$);

($e_3$) determining new values of the or each piece of representative information ($\Gamma_{g,i}$, $W_i$) to minimize the residual ($L_0$);

step (e) including, at each iteration, ($e_4$) calculating the average ($\hat{E}_k^0$), for each energy, of an estimated number of counts ($\hat{n}_k^0$) for each interval ($I_i$) based on the representative information ($\Gamma_{g,i}$, $W_i$) determined in a preceding iteration, the residual ($L_0$) calculated in step ($e_2$) comprising a second criterion ($C_2$) calculated from probabilities according to a given statistical law to measure, for each energy, an average number of counts ($n_k^0$), the Poisson law being parameterized based on the average ($\hat{E}_k^0$) calculated in step ($e_4$);

and further comprising scanning the raw representative information ($\Gamma_{g,i}$(free), $W_i$(free)) obtained at the end of step (e) at each interval ($I_i$) to determine the raw representative information coming from a given interval of physical values ([a, b]), then blocking at least one piece of raw representative information ($x_i$) coming out of the interval of physical values so that its value ($x_L$) remains equal to one end of the interval, the method then comprising a step (f) for determining each piece of representative information ($\Gamma_{g,i}$, $W_i$) in each interval through successive iterations until verification of a convergence criterion, each iteration comprising:

($f_1$) estimating a number of counts ($\hat{n}_{k,i}(\underline{x}_b)$) received at each energy in each interval based on the representative information determined at a preceding iteration from representative information obtained after blocking the or each piece of locked representative information;

($f_2$) calculating a residual ($L_3$) comprising a third criterion ($C_3$) calculated from probabilities according to Poisson law to measure, for each energy, the number of estimated counts ($\hat{n}_{k,i}(\underline{x}_{free})$) at each interval from representative information obtained without blocking at the end of step (e), the Poisson law being parameterized based on the number of counts $\hat{n}_{k,i}(\underline{x}_b)$ estimated in step ($f_1$) at each interval.

\* \* \* \* \*